United States Patent
Jung et al.

(10) Patent No.: US 10,641,719 B2
(45) Date of Patent: May 5, 2020

(54) RECRYSTALLIZATION RATE MEASUREMENT METHOD OF ZIRCONIUM ALLOY CLADDING OF NUCLEAR FUEL ROD USING EBSD PATTERN QUALITY

(71) Applicants: Tae Sik Jung, Daejeon (KR); Yong Kyoon Mok, Daejeon (KR); Yoon Ho Kim, Daejeon (KR); Chung Yong Lee, Daejeon (KR); Hun Jang, Sejong-si (KR)

(72) Inventors: Tae Sik Jung, Daejeon (KR); Yong Kyoon Mok, Daejeon (KR); Yoon Ho Kim, Daejeon (KR); Chung Yong Lee, Daejeon (KR); Hun Jang, Sejong-si (KR)

(73) Assignee: KEPCO NUCLEAR FUEL CO., LTD., Daejeon (KR)

(*) Notice: Subject to any disclaimer, the term of this patent is extended or adjusted under 35 U.S.C. 154(b) by 0 days.

(21) Appl. No.: 16/041,335

(22) Filed: Jul. 20, 2018

(65) Prior Publication Data

US 2019/0154600 A1    May 23, 2019

(30) Foreign Application Priority Data

Nov. 17, 2017  (KR) .................... 10-2017-0154196

(51) Int. Cl.
*G01N 23/2251*    (2018.01)
*G01N 23/203*     (2006.01)
*G01N 33/20*      (2019.01)

(52) U.S. Cl.
CPC ....... *G01N 23/2251* (2013.01); *G01N 23/203* (2013.01); *G01N 33/20* (2013.01);
(Continued)

(58) Field of Classification Search
CPC .. G01N 23/2251; G01N 33/20; G01N 23/203; G01N 2223/0561; G01N 2223/053
See application file for complete search history.

(56) References Cited

U.S. PATENT DOCUMENTS 9,002,499 B2    4/2015 Raghavan et al.
2018/0237882 A1*  8/2018 Unno ................. C21D 1/76

FOREIGN PATENT DOCUMENTS

KR    1020040090662 A    10/2004
KR     100660209 B1     12/2006
(Continued)

OTHER PUBLICATIONS

R.J. McCabe, D.F. Teter, "Analysis of recrystallized volume fractions in uranium using electron backscatter diffraction," J. Microsc., 223 (Jul. 1, 2006), pp. 33-39.*
(Continued)

*Primary Examiner* — Brooke Purinton
(74) *Attorney, Agent, or Firm* — Reinhart Boerner Van Deuren P.C.

(57) ABSTRACT

The present invention relates to a recrystallization rate measurement method of zirconium alloy cladding of a nuclear fuel rod, the method including: step 1 of irradiating SEM electron beams at a given scanning interval onto a first specimen to a third specimen which were electrolytically polished and obtaining electron backscattered signals therefrom by an EBSD camera; step 2 of converting electron backscattered signals obtained in step 1 into pattern quality values, respectively, and generating the pattern quality values as frequencies by a specified interval; step 3 of obtaining pattern quality frequencies (B+D) which are a portion of a whole frequency distribution of the second specimen, and pattern quality frequencies (D+E) which are a portion of a whole frequency distribution of the first specimen; and step 4 of obtaining the recrystallization rate of the second specimen with an equation of $$X' = \frac{(B+D)}{(D+E)} \times 100, \%.$$

4 Claims, 7 Drawing Sheets

(52) U.S. Cl.
CPC .......... *G01N 2223/053* (2013.01); *G01N 2223/0561* (2013.01); *G01N 2223/418* (2013.01); *G01N 2223/602* (2013.01)

(56) References Cited

FOREIGN PATENT DOCUMENTS

| KR | 101112027 A | 2/2011 |
|----|-------------|--------|
| KR | 101493944 B1 | 2/2015 |

OTHER PUBLICATIONS

Hang Tian et al.; Recrystallization behavior of cold-rolled Zr—1Nb Alloy; 2015, 8 pages; Journal of Nuclear Materials 456 (2015) 321-328.
Yang-Il Jung et al.; "Behavior of a recrystallization . . . "; 2009; 4 pages; Journal of Alloys and Compounds 479 (2009) 423-426.
J. Tarasiuk et al.; Estimation of recrystallized volume fraction from EBSD data; 2002; 11 pages; Acta Materialia 50 (2002) 1467-1477.
Gulshan Kumar et al.; Defining the stages of annealing in a moderately deformed commercial Zirconium alloy; 2015; 10 pages; Journal of Nuclear Materials 466 (2015) 243-252.

\* cited by examiner

<3 dimensional Image Quality distribution chart>

RECRYSTALLIZATION RATE MEASUREMENT METHOD OF ZIRCONIUM ALLOY CLADDING OF NUCLEAR FUEL ROD USING EBSD PATTERN QUALITY

CROSS REFERENCE TO RELATED APPLICATION

The present application claims priority to Korean Patent Application No. 10-2017-0154196, filed Nov. 17, 2017, the entire contents of which is incorporated herein for all purposes by this reference.

FIELD OF THE INVENTION

The present invention relates generally to a recrystallization rate measurement method of metal and, more particularly, to a recrystallization rate measurement method of zirconium alloy cladding of a nuclear fuel rod using EBSD pattern quality.

BACKGROUND OF THE INVENTION

Generally, metal products used in industry are made into shapes suitable for use through final cold work before being final products, and come to have characteristics satisfying product performance requirements through final heat treatment.

These product characteristics are directly related to a state of grains forming a microstructure, and are determined by microstructural changes caused by the final heat treatment applied after cold working.

Accordingly, the final heat treatment in terms of producing the product is the last step capable of controlling the material characteristics of the product.

Effects of the final heat treatment affecting the product characteristics may be described in detail as follows.

The cold working of a final heat treated product causes macroscopically the deformation of the grains composing the microstructure by forcing the atoms to move in a short time duration without gaining thermal assistance.

Microscopically, the generation and transfer of dislocation for deformation begins in the grains, and an increase of dislocation density due to subsequent continuous processing destroys the interatomic arrangement and eventually renders the microstructure disordered to such an extent that the grains and grain boundaries cannot be distinguished. A material composed of such a wrought structure is no longer capable of generating and transferring the dislocation, thereby having a high mechanical strength with a low percent elongation. Accordingly, improvement through heat treatment is required due to the low percent elongation.

That is, defects in the deformed grains showing embrittlement characteristics are extinguished or existing grains are replaced with newly formed defect-free grains through the heat treatment, whereby softening characteristics are added to the material.

These phenomena are called recovery and recrystallization, respectively, and generally the recrystallization occurs at relatively higher temperatures compared with the recovery. The recrystallization is expressed as a quantitative fraction called recrystallization rate which is mainly used as a heat treatment target or a material characteristic parameter capable of predicting the behavior of a material.

Eventually, the fraction of the total volume of the existing recrystallized grains can be expressed as the recrystallization rate, and this fraction is also expressed as a ratio of mechanical strength. In reality, the recrystallization rate of materials is evaluated in industry using two conventional methods as below.

A first method called recrystallization volume fraction measurement method generally uses micrographs taken by using Transmission Electron Microscopy (TEM). At this time, a fraction, $S_{Rex}/S_{total}$ of the total two dimensional area $S_{total}$ versus the recrystallized grain area $S_{Rex}$ is defined as the recrystallization rate by using a method of a two-dimensional measurement of the three-dimensional space in the same manner as a general grain size measurement.

However, due to the nature of TEM micrographs, the maximum observable range for observing grains is so narrow in units of several tens of micrometers that information provided therein is insufficient to represent the material. In addition, the criterion for determining recrystallized grain and cold worked grain is ambiguous, whereby a result slightly different from the actual recrystallization rate value may be obtained.

A second method called mechanical strength measurement method is usually calculated using the yield strength. Specifically, the yield strength $Y_{min}$ obtained by a uniaxial tensile test after completely recrystallizing the cold worked material by heat treatment is set to a 100% recrystallization rate, and the yield strength $Y_{max}$ of the material in a state without heat treatment is set to a 0% recrystallization rate. Accordingly, since the yield strength $Y_p$ of the partially recrystallized material lies between 0 and 100% recrystallization rates, an amount of strength decreased from $Y_{max}$ relative to a difference between $Y_{max}$ and $Y_{min}$ is calculated as the recrystallization rate $X_Y$,rex of the material as shown in Equation 1 below.

$$X_{Y,rex} = \frac{Y_{max} - Y_p}{Y_{max} - Y_{min}} \times 100, \%  \quad \text{[Equation 1]}$$

The yield strength is a result due to many grains, thereby being representable information of the microstructure state. However, in the case of a material heat-treated at a temperature of recrystallization temperature $T_{rex}$ or lower, a calculation result may be caused to be far away from the actual recrystallization rate because the reduction in strength is mainly due to the recovery rather than due to a formation of recrystallized grains.

Generally, recrystallization temperature $T_{rex}$ of zirconium alloy cladding of a nuclear fuel rod is about 500° C. In fact, papers dealing with the recrystallization rate modeling through the measurement of the yield strength of zirconium alloys show that the experiment has been performed excluding the cases of zirconium alloys heat-treated at 500° C. $T_{rex}$ or lower [Hang Tian et al., J. Nucl. Mater. 456 (2015) p. 321, Y. I. Jung et al., J. Alloys Comp. 497 (2009) p. 423].

This is attributable to inappropriate results produced from recrystallization rate modeling calculations by a reduction in strength due to the recovery rather than by a reduction in strength caused by thermally-induced recrystallization.

Since the final heat treatment temperature of zirconium alloy cladding of nuclear fuel rods used in nuclear power plants is 500° C. or less, nuclear fuel manufacturers use TEM micrographs to measure the recrystallization rate of zirconium alloy cladding. In general, a TEM micrographs is allowed to observe local areas only in the range of up to tens of square microns, whereby a number of multiple TEM micrographs are required to demonstrate the typical recrystallization rate of heat-treated specimens.

In Korean Patent No. 10-1493944, after selecting a critical value by measuring an crystal orientation spread value of a metal material by using EBSD, the recrystallization rate is measured through a process comparing the critical value with crystal orientation spread values of the crystal grains of a specific size or larger.

In U.S. Pat. No. 9,002,499, a method is proposed to determine a degree of the recovery by measuring azimuth of crystal grains of a metal material by using EBSD.

Up to now, the recrystallization rate measurement method by using EBSD, like the existing registered patents, has stated various analytical methods capable of determining whether a grain is recrystallized or not according to an azimuth difference after measuring crystallographic orientations of the grains. In addition, much literature has also reported methods for determining recrystallized grains based on crystallographic orientation.

A problem associated with these methods is that in order to determine whether a measured grain is recrystallized or not, it is necessary to set the critical crystal orientation spread value and minimum effective grain size as references through a basic experiment. In other words, when the two critical values above are set incorrectly, there is a possibility to get values different from the actual recrystallization rate of the material.

Therefore, there is a need for a technique that can identify not only occurrence of the recrystallization rather than the recovery but also a degree the recrystallization rate has progressed with a high accuracy without passing through precise measurements which entail numerous trials and errors.

The foregoing is intended merely to aid in the understanding of the background of the present invention, and is not intended to mean that the present invention falls within the purview of the related art that is already known to those skilled in the art.

BRIEF SUMMARY OF THE INVENTION

Accordingly, the present invention has been made keeping in mind the above problems occurring in the related art, and the present invention is intended to provide a more stable and accurate calculation method compared with an existing calculation method of a recrystallization rate of zirconium alloy cladding of a nuclear fuel rod in various temperature intervals by using pattern quality values measured by utilizing EBSD.

In order to achieve the above object, according to one aspect of the present invention, there is provided a recrystallization calculation method of zirconium alloy cladding of a nuclear fuel rod using EBSD pattern quality, the method including: irradiating SEM electron beams at a given scanning interval onto a completely recrystallized first specimen, a partially recrystallized second specimen to be measured for recrystallization rate, and an as-deformed third specimen which were electropolished and obtaining electron backscattered signals therefrom by an EBSD camera (step 1); converting the electron backscattered signals obtained from the first specimen to the third specimen into pattern quality values, respectively, by using an EBSD software and generating the pattern quality values as frequencies by a specified interval (step 2); obtaining pattern quality frequencies (B+D) deviated from the frequency distribution of the third specimen among a whole frequency distribution of the second specimen, and pattern quality frequencies (D+E) deviated from the frequency distribution of the third specimen among a whole frequency distribution of the first specimen (step 3); and obtaining the recrystallization rate of the second specimen with an equation of $$X' = \frac{(B+D)}{(D+E)} \times 100, \%$$

(step 4).

Here, an area which SEM beams are entered into each of the first specimen to the third specimen in step 1 is 100 μm×100 μm.

In addition, the fixed scanning interval in step 1 is 200 to 300 nm.

In addition, the interval of the pattern quality values in step 2 is 100 to 1,000.

With the recrystallization rate calculation method of zirconium cladding of a nuclear fuel rod using EBSD according to the present invention, it may reinforce both of the inaccurate recrystallization rate calculation using mechanical strength caused by the strength reduction due to recovery when heat-treated at the recrystallization temperature or lower, and the possibility of obtaining insufficient recrystallization information due to observation of local areas when TEM micrographs are utilized. In addition, a more accurate recrystallization rate can be obtained compared to a recrystallization rate calculation method using existing pattern quality.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Specific structures or functional description presented in an embodiment of the present invention are merely illustrative for the purpose of describing the embodiment according to the concept of the present invention, and embodiments according to the concept of the present invention can be implemented in various forms. In addition, the embodiments should not be construed as limited to the embodiments set forth herein, but should be understood to include all modifications, equivalents, and alternatives falling within the spirit and scope of the present invention.

Hereinbelow, exemplary embodiments of the present invention will be described in detail with reference to the accompanying drawings. Throughout the drawings, the same reference numerals will refer to the same or like parts.

As described in a section of Description of the Related Art above, obtaining a precise and stable recrystallization rate calculation using a recrystallization rate measurement method through setting of critical values of a crystal orientation of grain and a minimum crystal grain size is difficult.

Accordingly, a value called pattern quality obtainable from EBSD is introduced in a recrystallization rate calculation in the present invention.

The pattern quality represents sharpness value of a Kikuchi line, wherein the Kikuchi line is an electron beam of a Scanning Electron Microscopy (SEM) coming out by backscattered diffraction from a specimen after entering thereinto. Meanwhile, recrystallization rate can be calculated by comparing pattern quality values of a partially crystallized specimen (second specimen) with pattern quality values of a completely recrystallized specimen (first specimen) and an as-deformed specimen (third specimen).

A calculation method through obtaining the pattern quality value has been introduced only for copper alloy in an existing literature [Tarasiuk et al., Acta Mater. 50 (2002) p. 1467]. However, there is a problem that the corresponding calculation method cannot obtain an accurate recrystallization rate from the pattern quality distribution of zirconium cladding of a nuclear fuel rod.

Therefore, an improvement is necessary for the calculation method of recrystallization rate using the pattern quality is urgently needed.

Accordingly, a calculation method of the present invention will be described as below and validity thereof will be verified through an appropriate example.

Characteristics of EBSD provided in the SEM used in the present invention is as follows.

Arrangement of atoms composing a material is positioned in a different direction for each grain, and a short wavelength electron entered thereinto from an electron gun of the SEM comes out by diffraction from each of the grains, wherein the electron is recognized as a Kikuchi line by an EBSD detector. At this time, the Kikuchi line is stored as a pattern quality value representing a degree of sharpness through a self-calculation.

A clear Kikuchi line means the arrangement of atoms is extremely regular and indicates a corresponding measuring part has no defect by being recrystallized, thereby having a high pattern quality index. On the contrary, since arrangement of atoms of a wrought structure is disorderedly distributed and has many defects, it is difficult for the entered electron to be diffracted, whereby a blurred Kikuchi line appears resulting in obtaining a low pattern quality value.

Prior to describing a detailed calculation method of the recrystallization rate characterizing the invention, an obtaining method of a pattern quality value used as a calculation input value and obtained from EBSD may be described as follows.

The pattern quality value is a numerical result obtained by shooting an electron beam in the manner of scanning while moving by a specific interval within a designated area of a material surface being observed by the SEM. The pattern quality values contain information of the material surface scanned in the designated area and recrystallization rate is calculated with these values as an input value.

Figure 1:
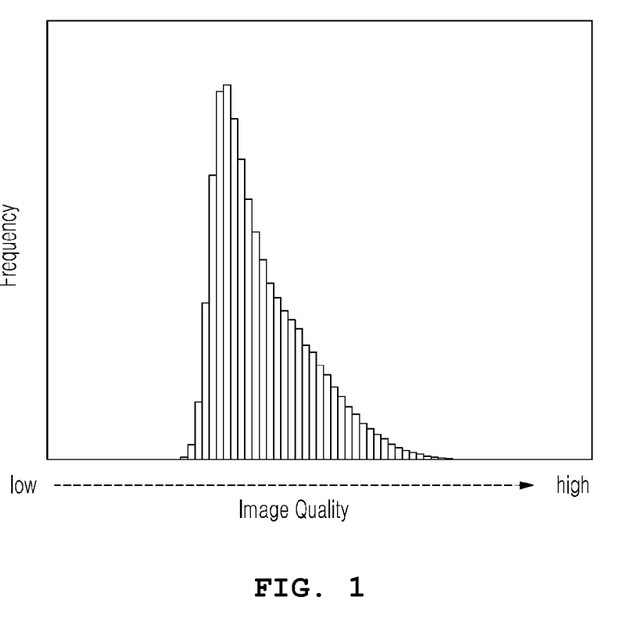
FIG. 1 is a histogram illustrating a frequency by each of specified intervals after categorizing pattern quality values of a heat-treated zirconium cladding according to an arbitrarily specified interval.

FIG. 1 illustrates a distribution of each pattern quality value in a form of a histogram by measuring the frequency by the corresponding interval after categorizing actual pattern quality values obtained from an arbitrary material according to an arbitrarily specified interval.

Figure 2:
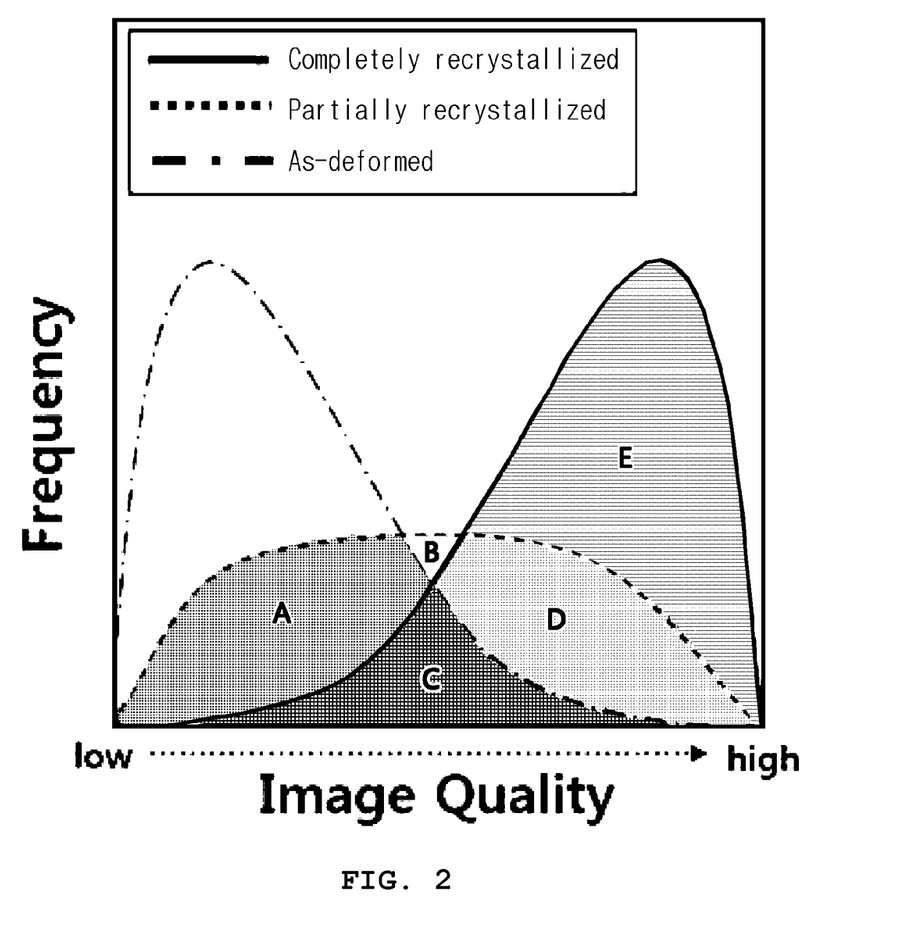
FIG. 2 illustrates schematic line graphs showing cumulative frequency, wherein areas enclosed by the line graphs are labeled into A, B, C, D, and E.

In FIG. 2, a frequency distribution trend corresponding to each of different recrystallization rates of an arbitrary material is illustrated in a schematic line graph by connecting frequency points corresponding to designated points of pattern quality values to each other, wherein areas overlapping each other or separated from each other are indicated as A, B, C, D, and E.

As a material is heat-treated more closely to be completely recrystallized as shown in FIG. 2, pattern quality values of the material are distributed skewed toward higher pattern quality value with the highest frequency.

Tarasiuk calculated a recrystallization rate X by taking the pattern quality as an input value using Equation 2 below:

$$X = \left\{ \left( \frac{B+D}{\text{Total measured frequency}} \right) \times \left[ 1 + \left( \frac{C-B}{\text{Total measured frequency}} \right) \right] \right\} \times 100, \% \quad \text{[Equation 2]}$$

Here, as shown in FIG. 2, B represents a total frequency of an area where the frequency of the pattern quality distribution of the partially recrystallized specimen is greater than that of the as-deformed specimen or the completely recrystallized specimen; C represents a total frequency of an area where three distributions overlap each other; D represents a total frequency of an area where the frequency of the pattern quality distribution of the partially recrystallized specimen is smaller than that of the completely recrystallized specimen but greater than that of the as-deformed specimen; E represents a total frequency of an area where the frequency of the completely recrystallized specimen is greater than that of the partially recrystallized specimen; and the Total measured frequency is a sum of all of A, B, C, and D.

First, in step 1 of the present invention, pattern quality values are obtained through EBSD using electrolytic polishing for zirconium cladding of a nuclear fuel rod, wherein the zirconium cladding is to be measured for recrystallization rate. Claddings used at this time were heat-treated for eight hours at 440, 460, 480, 500, 520, 540, 560, or 580° C. in a vacuum state, and an as-deformed specimen is measured together when EBSD is measured. At this time, a specimen heat-treated for eight hours at 580° C. may be utilized as a completely recrystallized reference specimen.

After heat-treatment, a surface perpendicular to axial direction of the cladding was mechanically polished, and a shiny surface was additionally made through electropolishing. While scanning was proceeded at 250 nm intervals for a part of 100 μm (width)×100 μm (length) on the surface, 185,031 electron backscattered signals per a specimen were received.

In step 2 of the present invention, after the measured electron backscattered signals of each of the specimens are converted into pattern quality values by using an EBSD software, the pattern quality values are categorized by an arbitrarily specified interval, and cumulatively generated as frequency by the specified interval. At this time, a maximum pattern quality value was 69,647, and the frequency of each corresponding interval was generated by dividing pattern quality values of each of specimens by 1,000.

Figure 3A:
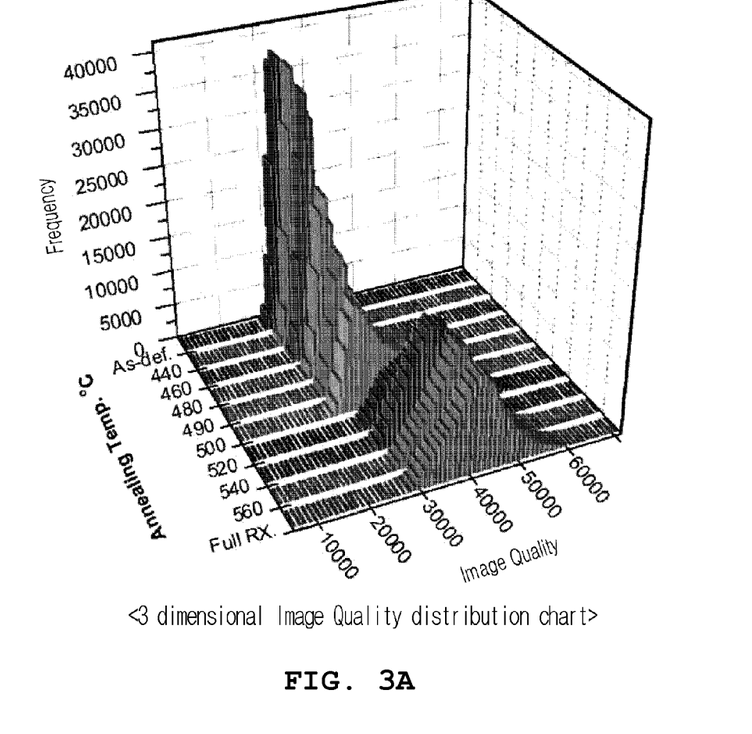
FIG. 3A and FIG. 3B illustrate pattern quality distribution charts measured through an embodiment for zirconium cladding heat-treated at various temperatures in a three dimensional histogram and two dimensional line graphs.
Figure 3B:
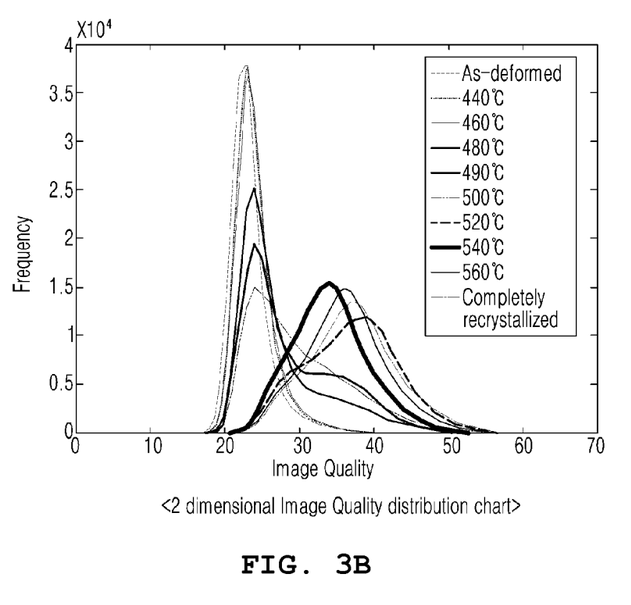

FIG. 3 expresses pattern quality values obtained at all heat treatment temperatures divided by intervals of 1000 and cumulative frequency values obtained at the corresponding intervals in a three dimensional histogram (FIG. 3A) and two dimensional line graph (FIG. 3B).

In step 3 of the present invention, frequencies corresponding to areas of B, D, and E in FIG. 2 are obtained, respectively, from the as-deformed, partially recrystallized, and completely recrystallized pattern quality distribution charts.

In step 4 of the present invention, calculation is performed according to Equation 3 with obtained frequencies of areas of B, D, and E, respectively.

$$X' = \frac{(B+D)}{(D+E)} \times 100, \% \quad \text{[Equation 3]}$$

deducting the contribution of the area B to the recrystallization in the calculation method of Tarasiuk.

Figure 5:
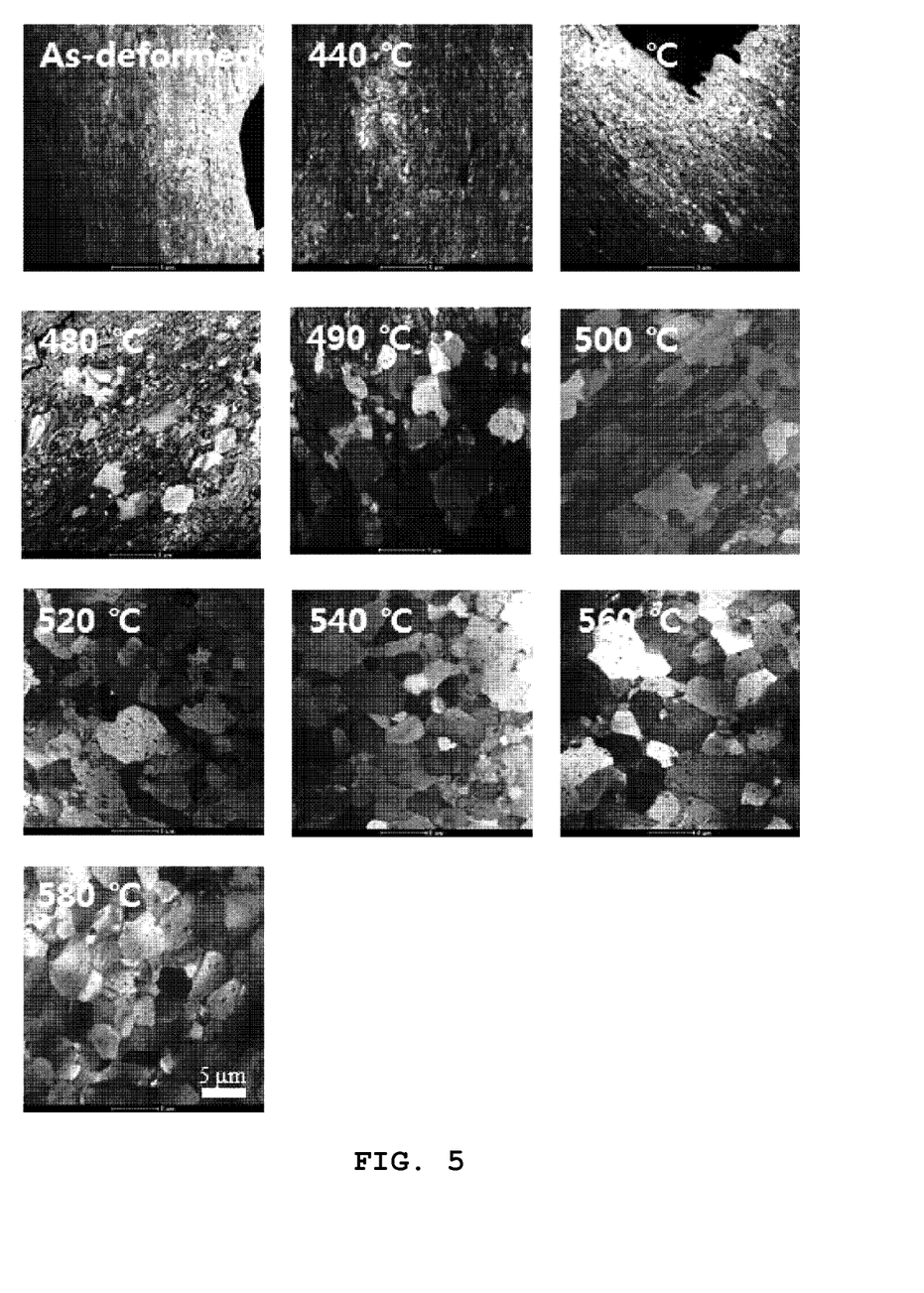
FIG. 5 illustrates photographs of grains of an embodiment observed by using a TEM at a magnification of 4,900 times.

Specifically, in the calculation method of Tarasiuk, the right term is reduced due to a high value of B, thereby reducing the recrystallization rate value. That is, the reduced recrystallization rate value is obtained at 540□ because it is not calculated for the area B being weighted the same as the area D in the relevant equation, though the area B is actually recrystallized. Since the TEM photograph at 540□ of FIG. 5 is the result to be surely judged that recrystallization fraction is 90% or greater, the calculation method of Tarasiuk does not seem to be a valid method for the zirconium alloy cladding.

Accordingly, the area B should be used with a same weighting as the area D in recrystallization rate calculation for the zirconium alloy cladding. Accordingly, an improved calculation equation is suggested as Equation 3.

Through the equation of the present invention, a recrystallization rate which is the ratio expressed as a percentage

TABLE 1

| | Heat treatment temperature, ° C. | | | | | | | |
|---|---|---|---|---|---|---|---|---|
| Calculation method | 440 | 460 | 480 | 490 | 500 | 520 | 540 | 560 |
| $X_{Y, rex}$ (Yield strength, Equation 1) | 45.6% | 51.9% | 61.4% | 75.9% | 84.3% | 94.7% | 94.8% | 96.4% |
| X (Tarasiuk 1st, Equation 2) | 11.4% | 14.0% | 36.2% | 48.1% | 52.0% | 92.1% | 76.9% | 91.3% |
| $X'$ (Present invention, Equation 3) | 12.5% | 15.9% | 41.1% | 53.7% | 59.7% | 97.4% | 95.2% | 99.3% |

Figure 4:
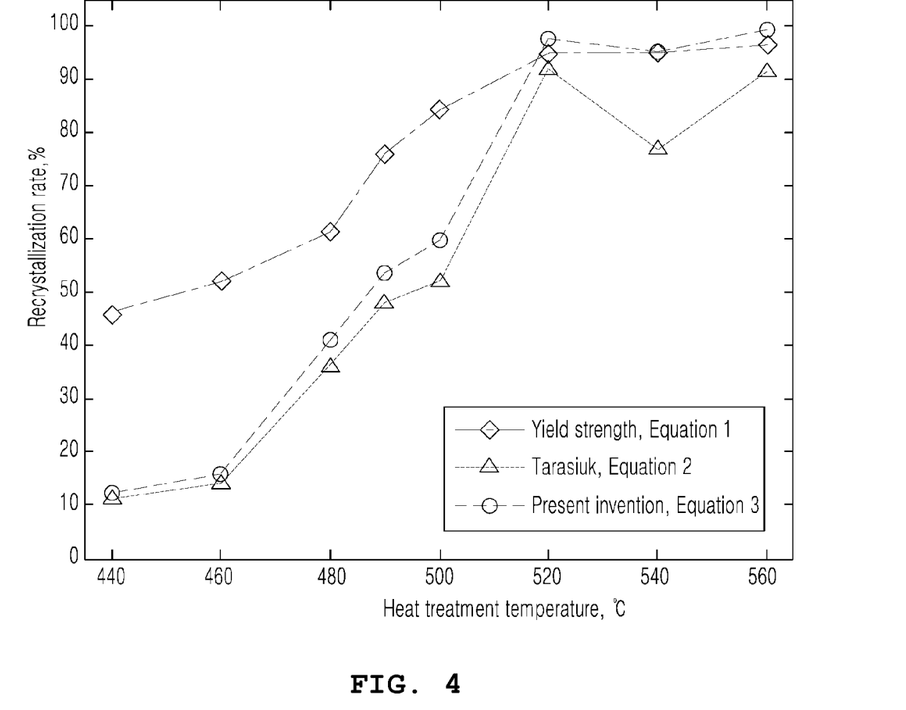
FIG. 4 illustrates line graphs for recrystallization rate values obtained using Equation 1 to Equation 3.

Table 1 expresses recrystallization rate values obtained by the calculation method of the present invention (Equation 3), the method introduced in the literature of Tarasiuk (Equation 2), and the calculation method through yield strength measurement value described in the section of Description of the Related Art together, and these recrystallization rate values are illustrated by heat treatment temperature in the line graphs of FIG. 4. In addition, FIG. 5 illustrates TEM micrographs of the measured specimens.

Recrystallization rate values inferred through the microstructure photographs of FIG. 5 are shown to have a large deviation from recrystallization rate values $X_{Y,rex}$ calculated from the yield strength in the case of the specimen heat-treated below 520□. However, the recrystallization rate values $X_{Y,rex}$ at 520□ or greater accord well with the recrystallization rate values inferred through the microstructure micrographs.

In FIG. 4, recrystallization rate values are shown to rise with increasing heat treatment temperature in line graphs, wherein the recrystallization rate values obtained by Tarasiuk equation (Equation 2) and the present invention equation (Equation 3), respectively, vary in an almost same trend at each temperature. However, at 540□, the result of Equation 2 is 76.9% which is approximately 18% lower than the results of Equations 2 and 3 of 94.8 and 95.2%, respectively.

Figure 6:
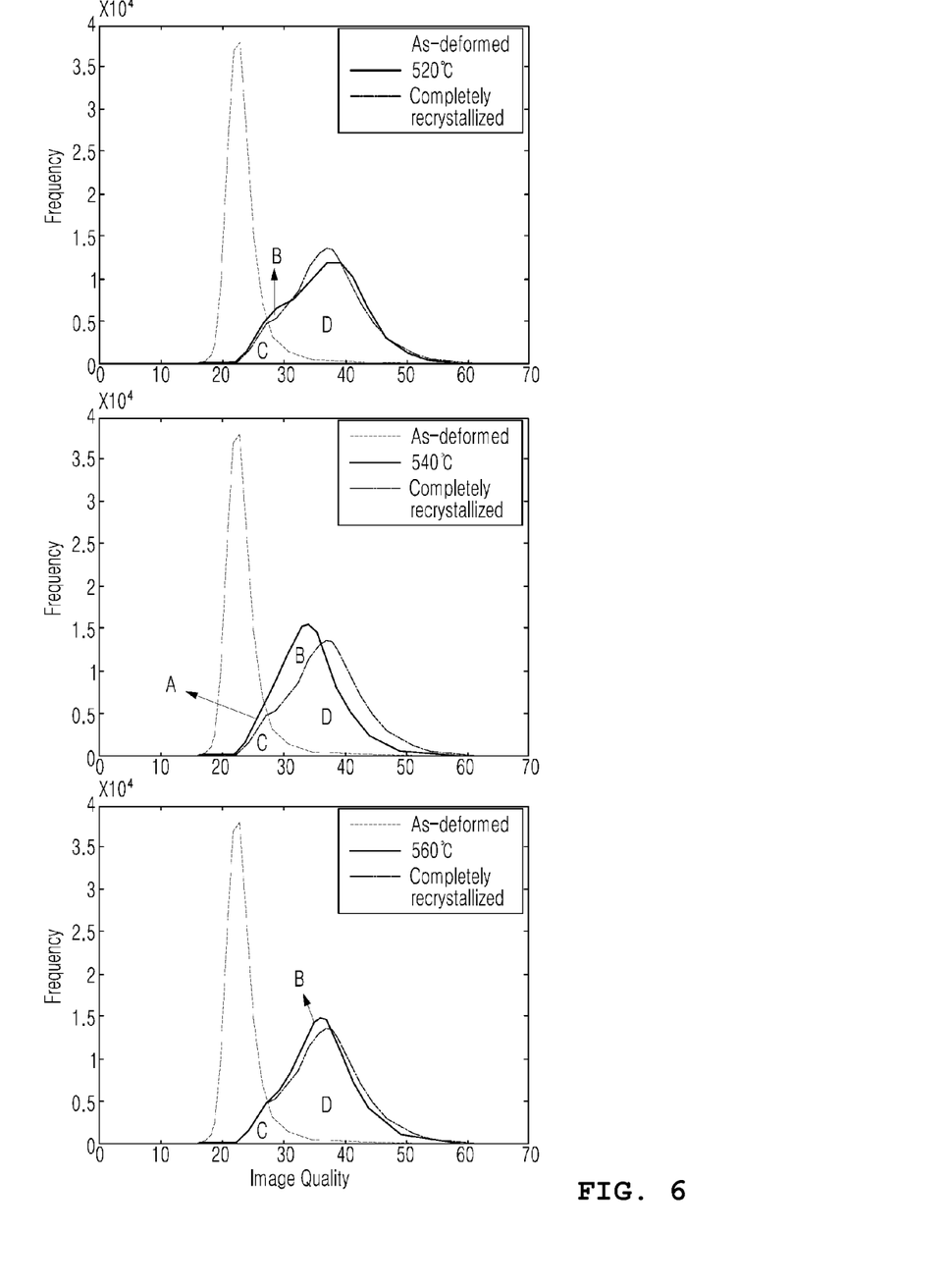
FIG. 6 illustrates line graphs each representing pattern quality distribution chart of a specimen at 520, 540, and 560□, respectively, with as-deformed and completely recrystallized specimens as references, respectively.

This tendency is not observed in the cases of 520□ and 560□, and a reason therefor may be described by comparing quality value distribution charts at 520, 540, and 560□ of FIG. 6. In FIG. 6, a graph at 540□ shows a larger frequency B and a smaller frequency D compared with a graph at 520□ or 560□. This phenomenon is arisen from heterogeneous recrystallization behavior of the zirconium alloy because abnormally grown grains emitting a signal for area D emit a signal for area B while being recrystallized in small crystal grains at a higher temperature [G. Kumar et al., J. Nucl. Mater. 466 (2015)]. That is, although crystal grains emitting a signal for area B are also crystal grains of a recrystallized area, it is set to calculate the recrystallization rate by is calculated by taking the completely recrystallized pattern quality frequency (D+E) deviated from the as-deformed pattern quality distribution as a denominator and the frequency (B+D) which is the partially recrystallized pattern quality frequency deviated from the as-deformed pattern quality distribution as a nominator.

The equation of the present invention may calculate an accurate recrystallization rate in a whole of temperature intervals without causing reduction of a recrystallization rate value in a specific temperature interval for measured recrystallization rate X' of zirconium alloy cladding of the nuclear fuel through an embodiment.

The present invention described as above is to be understood not to be limited to the aforementioned embodiment and accompanying drawings. Accordingly, it will be apparent to those having ordinary knowledge and skilled in the art the present invention pertains that various replacement, modifications, and variations are possible, without departing from the spirit or scope of the concept of the present invention.

What is claimed is:

1. A recrystallization rate measurement method of zirconium alloy cladding of a nuclear fuel rod, the method comprising:
   irradiating Scanning Electron Microscopy (SEM) electron beams at a given scanning interval onto a completely recrystallized first zirconium alloy specimen, a partially recrystallized second zirconium alloy specimen to be measured for recrystallization rate, and an as-deformed third zirconium alloy specimen which were electropolished and obtaining electron backscattered signals therefrom by an Electron Backscattter Diffraction (EBSD) camera (step 1);
   converting the electron backscattered signals obtained from the first zirconium alloy specimen to the third zirconium alloy specimen into pattern quality values, respectively, by using an EBSD software and generating the pattern quality values as frequencies by a specified interval (step 2);

obtaining pattern quality frequencies (B+D) deviated from the frequency distribution of the third zirconium alloy specimen among a whole frequency distribution of the second zirconium alloy specimen, and pattern quality frequencies (D+E) deviated from the frequency distribution of the third zirconium alloy specimen among a whole frequency distribution of the first zirconium alloy specimen (step 3); and obtaining the recrystallization rate, X', of the second zirconium alloy specimen with an equation of $$X' = \frac{(B+D)}{(D+E)} \times 100, \%. \qquad \text{(step 4)}$$

2. The method of claim 1, wherein an area which SEM beams are irradiated onto each of the first zirconium alloy specimen to the third zirconium alloy specimen in step 1 is 100 μm×100 μm.

3. The method of claim 1, wherein the given scanning interval in step 1 is 200 to 300 nm.

4. The method of claim 1, wherein the specified interval of the pattern quality values in step 2 is 100 to 1,000.

* * * * *